United States Patent
Bruening

(10) Patent No.: US 6,495,700 B1
(45) Date of Patent: Dec. 17, 2002

(54) PROCESS FOR PRODUCING PHENSERINE AND ITS ANALOG

(75) Inventor: Joerg Bruening, West Chester, PA (US)

(73) Assignee: Axonyx, Inc., New York, NY (US)

( * ) Notice: Subject to any disclaimer, the term of this patent is extended or adjusted under 35 U.S.C. 154(b) by 0 days.

(21) Appl. No.: 10/042,586

(22) Filed: Jan. 9, 2002

(51) Int. Cl.[7] ............................................. C07D 487/04
(52) U.S. Cl. ..................................................... 548/429
(58) Field of Search ......................................... 548/429

(56) References Cited

U.S. PATENT DOCUMENTS

| | | |
|---|---|---|
| 4,791,107 A | 12/1988 | Hamer et al. |
| 4,831,155 A | 5/1989 | Brufani et al. |
| 4,900,748 A | 2/1990 | Brossi et al. |
| 4,978,673 A * | 12/1990 | Meroni et al. ............... 514/411 |
| 5,077,289 A | 12/1991 | Glamkowski et al. |
| 5,177,101 A | 1/1993 | Glamkowski et al. |
| 5,187,165 A | 2/1993 | Hamer et al. |
| 5,206,260 A | 4/1993 | Hichens et al. |
| 5,302,721 A | 4/1994 | Wong et al. |
| 5,306,825 A | 4/1994 | Brufani et al. |
| 5,409,948 A | 4/1995 | Greig et al. |
| 5,455,354 A | 10/1995 | Wong et al. |
| 5,498,726 A * | 3/1996 | Lee et al. ..................... 548/429 |
| 5,541,216 A | 7/1996 | Hamer et al. |
| 5,547,977 A | 8/1996 | Hamer et al. |
| 5,550,253 A | 8/1996 | Hamer et al. |
| 5,550,254 A | 8/1996 | Hamer et al. |
| 5,621,114 A | 4/1997 | Hamer et al. |
| 5,639,892 A | 6/1997 | Hamer et al. |
| 5,663,190 A | 9/1997 | Hamer et al. |
| 5,665,880 A | 9/1997 | Lee et al. |
| 5,677,457 A | 10/1997 | Lee et al. |
| 5,705,657 A | 1/1998 | Maiorana et al. |
| 5,734,062 A | 3/1998 | Lee et al. |
| 5,998,460 A | 12/1999 | Brossi et al. |

OTHER PUBLICATIONS

Polonovski, *Bul. Soc. Chim.*, 19:46–59 (1916).

* cited by examiner

*Primary Examiner*—Joseph K. McKane
*Assistant Examiner*—Rebecca Anderson
(74) *Attorney, Agent, or Firm*—Gibbons, Del Deo, Dolan, Griffinger & Vecchione

(57) ABSTRACT

A process for preparing phenserine compounds which are known acetylcholinesterase inhibitors from physostigmine compounds by hydrolysis to form an eseroline compound which is then condensed with an isocyanate.

5 Claims, No Drawings

PROCESS FOR PRODUCING PHENSERINE AND ITS ANALOG

BACKGROUND OF THE INVENTION

Phenserine and phenserine analogs are known acetylcholinesterase inhibitors making them useful in the treatment of Alzheimer's diseases and as anti-inflammatory agents. Please note U.S. Pat. Nos. 5,306,825 and 5,734,062. Phenserine has been produced by the conversion of physostigmine salt such as physostigmine salicylate to eseroline which is then reacted in a organic solvent in the presence of a base catalyst at a basic pH with an isocyanate such as phenyl isocyanate to produce phenserine and it's analogs. This process has suffered from many disadvantages due to the fact that it involved numerous processing steps in producing the phenserine or its analogs from the physostigmine salt. This resulted in poor yields of phenserine with a relatively low purity.

In the first step of this reaction, the physostigmine salt is converted to the physostigmine free base and this free base is then hydrolyzed to eseroline by treatment with a base in an organic solvent. The eseroline base produced by this method, such as disclosed in U.S. Pat. No. 5,498,726, requires extensive work-up involving numerous steps to separate it from the reaction mixture so that it can be later converted to phenserine. In another method, the eseroline base was also prepared by reacting the physostigmine with a metal alkoxide in an alcohol such as disclosed in U.S. Pat. No. 5,306,825, or by hydrolysis of physostigmine in a water miscible organic solvent with aqueous sodium hydroxide or potassium hydroxide solution, such as disclosed in U.S. Pat. No. 4,978,673, European Patent 0298,202 or via its eseroline fumarate salt (*Heterocycles* 1987, 26:5 pages 1271–1275). In these processes it is necessary to neutralize the crude reaction mixture with mineral acids or organic acids such as disclosed in U.S. Pat. Nos. 4,978,673 and 5,498,726. It is also necessary to prevent oxidation of the eseroline base in the solution by either applying a vacuum to the reaction mixture or by carrying out the reaction under an inert atmosphere such as disclosed in U.S. Pat. Nos. 5,306,825 and 5,498,726. These processes require isolation of the eseroline base from the reaction mixture in which it was formed leading to significant degradation unless strict precautions are taken to exclude air. Therefore, it has been long desired to provide an easy method for converting physostigmine salt to eseroline so that the eseroline can be converted to phenserine.

In the next step of this reaction, eseroline is reacted with an isocyanate to produce phenserine or a derivative thereof. This reaction is generally carried out in the presence of water immiscible organic solvents such as ethyl ether, diisopropyl ether, benzene, toluene or petroleum ether in the presence of traces of an alkaline substance such as an alkali metal hydroxide. Please note U.S. Pat. Nos. 4,978,673, 5,306,828 and 5,498,726. Other U.S. patents, such as U.S. Pat. Nos. 5,705,657 and 5,726,323 describe the use of quaternary phosphonium salts and quaternary ammonium salts with a metal cyanate or bicyclic amidine catalyst for the formation of phenserine. This process has been flawed with difficulties especially with regard to the isolation and purification of phenserine or its derivatives.

SUMMARY OF THE INVENTION

In accordance with this invention, phenserine and phenserine analogs of the formula

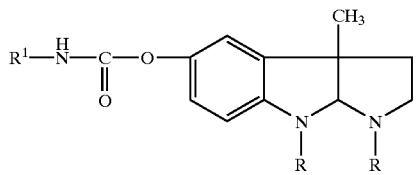

wherein R is a lower alkyl and $R^1$ is lower alkyl, phenyl, phenyl lower alkyl, cycloalkyl, or cycloalkyl lower alkyl;

are prepared from physostigmine compounds of the formula

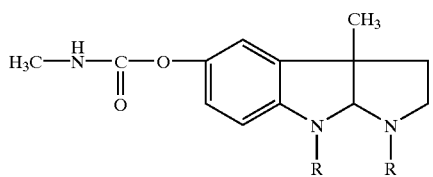

wherein R is as above;

or a salt thereof, via an eseroline compound of the formula:

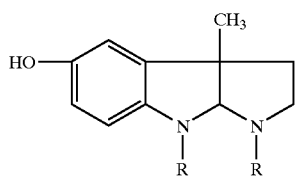

wherein R is as above;

by reacting the compound of formula II with an isocyanate of the formula:

$$R^1-N=C=O \qquad V$$

wherein $R^1$ is as above;

via a unique selection of reaction conditions, solvents and processing conditions which allow the phenserine compounds of Formula III to be produced in an economic manner in high yields and in a highly purified form. This is accomplished without the necessity of utilizing a large number of processing steps. Therefore, the use of this process makes it ideally suited for large scale production of phenserine and its analogs in a highly efficient and economic manner.

DETAILED DESCRIPTION OF THE INVENTION

The process of this invention is carried according to the following reaction scheme

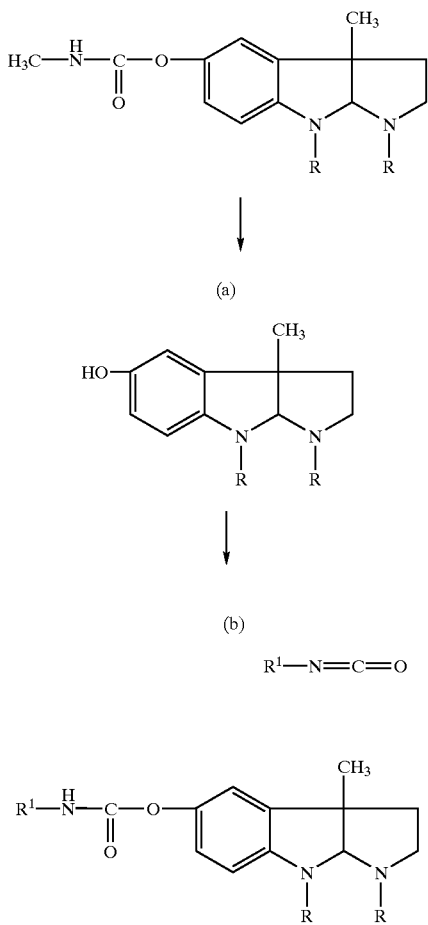

wherein R and $R^1$ are a lower alkyl and phenyl, phenyl lower alkyl or cycloalkyl, lower alkyl.

In accordance with the process of this invention the physostigmine compound of Formula I or it's salt is reacted to form the eseroline compound of Formula II by hydrolyzing the physostigmine compound of Formula I with an alkali metal hydroxide, in an aqueous reaction medium. The eseroline compound of Formula II is then isolated in pure form, from the aqueous reaction medium.

The purified eseroline is then treated with a strong organic base in an anhydrous reaction medium containing a water miscible organic solvent. The treated eseroline compound is then reacted, without isolating it from the said reaction medium, with an isocyanate of the formula V. This reaction is carried out by mixing said isocyanate compound of formula V with said eseroline compound in said reaction medium to form said phenserine compound of formula III. Thereafter the reaction is quenched by addition of water, allowing phenserine compound of formula III to be easily isolated in pure form. In this addition, the water can be added to the reaction mixture or the reaction mixture can be added to water. Generally it is preferred to add the reaction mixture to water.

This process can be utilized to make any of the enantiomers of Formula III, i.e., the (+) or (−) enantiomer, as well as, the racemate thereof. Depending upon the particular enantiomer of Formula I used a starting material, the compound of Formula II and III will be produced having the same stereoconfiguration at the quarternary chiral center of the compound of Formula I. On the other, the compound of Formula I can be used as a racemate to produce the compound of Formula II and III as racemates.

In the first step of the reaction of this invention, step (a), the physostigmine compound or salt thereof of Formula I is converted to the eseroline compound of Formula II. This reaction is a hydrolysis reaction carried out in the presence of an alkali metal hydroxide. Physostigmine is a compound which undergoes significant deterioration and therefore is used in the form of an acid addition salt. In accordance with the prior procedures when the physostigmine salt of Formula I is hydrolyzed to the eseroline compound of Formula II, the physostigmine salt is first converted to a free base and thereafter hydrolyzed.

In accordance with this invention the physostigmine salt of Formula I is hydrolyzed in one step without the need for conversion to its free base. This is accomplished by carrying out the hydrolysis with an alkali metal hydroxide in an aqueous medium. In carrying out this reaction any alkali metal hydroxide can be utilized. If desired, the aqueous solution may contain the compound of Formula I or, more preferably, contain this compound in the form of its salt. If desired, this aqueous solution can also contain a water immiscible organic solvent. Any conventional water immiscible organic solvent which is inert in this hydrolysis reaction can be utilized. Among the preferred solvents are included lower alkyl ethers such as ethyl ether, t-butylmethyl ether and diisopropyl ether. In carrying out this reaction temperature and pressure are not critical. This reaction of step (a) can be carried out at room temperature. However, generally temperatures from about 20°–50° C. are utilized in carrying out this reaction. In carrying out step a) it is important that no water miscible organic solvents be used in the hydrolysis. In this way the hydrolysis reaction and recovery of the compound of Formula II is carried out in absence of any water miscible organic solvents. By this procedure, there is a direct conversion of the acid addition salt of Formula I into the eseroline compound of Formula II without the necessity of converting the salt of Formula I into the free base of Formula I. In addition the eseroline compound of Formula II can be easily isolated from the reaction medium in pure form.

The presence of water and no water miscible organic solvents during the reaction of step (a) allows the eseroline base of Formula II to form in the aqueous medium in which it is soluble. In this manner the eseroline compound of Formula II can be recovered easily in pure form with high yields from the aqueous medium in which it is formed by simple and direct means. The purity of the eseroline base of Formula II can be from 90% or higher in many cases, from 98–99.9% purity.

While the recovery can be preferably carried at any basic pH level, it is generally carried out in accordance with this invention at pH range of from 8.0 to 9.5 which minimizes the loss of the eseroline base. The reaction of step (a) is carried at higher pHs. Generally the pHs are from 12 to 14. In this manner the eseroline compound of formula II is solubilized in the aqueous reaction medium so that it can be easily recovered. After the formation of the compound of formula II in the aqueous reaction medium, the pH can be adjusted to a pH of from 8.0 to 9.5 where the compound of formula II can be extracted in pure form. Any conventional means of extraction can be utilized to achieve this purpose. As stated hereinabove, the adjustment of the pH to 8.0 to 9.5 minimizes any loss of the eseroline compound of formula II.

In adjusting the pH from 8.0 and 9.5, we found that excellent results are achieved through the addition of an alkali metal bisulfite rather than using a mineral acid. In accordance with this invention, it has been found that mineral acids deleteriously affect the yield of the compound of formula II. This deleterious effect is eradicated when the pH for extraction is lowered to from 8.0 to 9.5 by means of an alkali metal bisulfite.

The term "pharmaceutically acceptable salts" refers to acid addition salts. The expression "pharmaceutically acceptable acid addition salts" is intended to apply to any non-toxic organic or inorganic acid addition salt of the compounds of Formula I and III. In accordance with this invention, any pharmaceutically acceptable salt of the compound of Formula I can be utilized as the starting material with the preferred salt being a salicylate salt. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hyroxymaleic, benzoic, hydrocybenzoic, pheynlacetic, cinnamic, salicylic, 2-phyenoxybenzoic, and sulfonic acids such as p-toluenesulfonic acid, methanesulfonic acid and 2-hydroxyethanesulfonic acid. Such salts can exist in either a hydrated or substantially anhydrous form.

In the next step of the process of this invention (step (b)), the eseroline compound of Formula II is converted to the phenserine compound of Formula III by reaction with the isocyanate of Formula V. This reaction is carried by first treating the purified eseroline compound of Formula II, after isolation from the reaction medium in which it was formed, with a strong organic base in an anhydrous reaction medium containing an inert aprotic water miscible organic solvent. By treating the compound of Formula II with the organic base in an inert aprotic water miscible organic solvent, the compound of Formula II is deprotonated to produce the reactive form of this compound. In this manner, the hydrogen from the hydroxy group is removed from the compound of Formula II and the compound is in position to react with the isocynate of Formula V. The formation of the reactive form of the compound of Formula II is carried out in an anhydrous medium utilizing an inert aprotic water miscible organic solvent with catalytic amounts of the organic base. Any conventional strong organic base as lower alkyl lithium, i.e., N-butyl lithium, can be utilized. Any water miscible aprotic organic solvent such as dimethoxyethane, tetrahydrofuran, etc. can be utilized. It must be remembered that the solvent must be inert to the deprotonation reaction medium as well as to the reaction medium in which the isocyanate of Formula V is utilized which includes the isocyanate itself.

In the next step of this process after the deprotonation has occurred, the deprotonated compound of Formula II is reacted with the isocyanate of Formula V to form the compound of Formula III. The isocyanate of Formula III is mixed with the reaction mixture in which the deprotonation occurs either by adding the reaction mixture containing the deprotonated compound of Formula V to the isocyanate of Formula V or by adding the isocyanate of Formula V to this reaction mixture.

In carrying out the reaction of step (b) with the isocyanate of Formula V one can utilize the same reaction medium utilized for the deprotonation reaction. In carrying out both the deprotonation and the later condensation with the isocyanate of Formula V, temperature and pressure are not critical and this reaction can be carried out at room temperature and atmospheric pressure. On the other hand temperatures from 15° to 30° C. are generally utilized. After mixing with the isocyanate of Formula V, the reaction can be quenched by the addition of water. Upon this addition of water the compound of Formula III precipitates from the resulting reaction medium making it easy to isolate and purify this compound. In this manner, the reaction mixture can be added to water or vice versa. In this manner, the phenserine compound of Formula III, in the form of its free base, can be isolated as a solid by precipitation from the reaction medium through the addition of or into water without any distillation or drying steps. In this manner the phenserine base is produced and can be recovered in high yields with a high degree of purity.

If it is desired to produce the phenserine as a salt for administration, the phenserine compound of Formula I can be converted to its phenserine acid addition salts by any suitable means such as through the reaction with a pharmaceutically acceptable acid such as the acids mentioned hereinabove. The preferred salt for administration of the phenserine compound of Formula I is phenserine tartarate or succinate.

The term "lower alkyl" includes all lower alkyl groups containing one to six carbon atoms such as methyl, ethyl, propyl and butyl, isobutyl, etc. The term "lower alkoxide" includes alkoxides of lower alkyl groups such as methoxide, ethoxide, isopropoxide and butyloxide. The term "cycloalkyl" includes cycloaklyl groups containing from 3 to 7 carbon atoms such as cyclopropyl, cyclobutyl, cyclohexyl.

The invention is further illustrated by the following examples which are only for illustrative purposes and not limitative thereof.

EXAMPLES

Examples 1

Eseroline Base Synthesis

Under an argon atmosphere, a 50 wt % sodium hydroxide solution (67.7 g, 0.8462 mol) was added dropwise to a slurry of physostigmine salicylate (100 g, 0.2418 mol) in degassed DI water (300 mL) at 45° C. During the addition the temperature was kept between 45 and 55° C. After about 3 hours at 45° C. the yellow solution was cooled to 25 to 30° C. and tert.-butyl methyl ether (300 mL) was added. The pH of the aqueous phase was adjusted to 9.1 with an aqueous solution of sodium meta bisulfite (54 g, $Na_2S_2O_5$, 250 mL water). The mixture was stirred for 30 minutes, the phases were allowed to settle and then separated. The aqueous phase was extracted twice for 30 minutes each with tert.-butyl methyl ether (300 mL each). The organic phases were combined and washed three times with 20 wt % sodium chloride solution (200 mL each), then dried over magnesium sulfate (150 g) overnight. The slurry was filtered through Celite and the filter cake washed with tert.-butyl methyl ether. The filtrate was concentrated to 300 mL at 25 to 29 in of vacuum and the residue co-distilled twice with diethoxymethane (300 mL each). The residue was diluted with diethoxymethane (300 mL) and heated to 50° C. The obtained light slurry was cooled to 5° C., stirred for 45 minutes, then concentrated to about 300 mL. Cold heptane (300 mL) was added dropwise, the slurry stirred for 20 minutes and the volume increased by addition of cold heptane (125 mL). After stirring for about 2 hours the slurry was filtered via a Buchner funnel. The collected solid was washed with cold heptane (200 mL) then dried in vacuo overnight. Eseroline base (35.6 g) was obtained as a white solid in 67.4% yield and 98.3% purity.

Example 2

Phenserine Base Synthesis

Eseroline base (50 g, 0.229 mol) was dissolved in 400 mL anhydrous dimethoxyethane under an argon atmosphere. Catalytic amounts of 2.5 M n-butyl lithium in hexanes (6.4 mL, 16 mmol) were added within 1 minute and the solution stirred for 10 minutes. Phenyl isocyanate (27.269 g, 0.2286 mmol) was added over 32 minutes keeping the temperature between 20 and 23° C. The reaction solution was stirred at r.t. for 2 hours 20 minutes, then transferred to an addition funnel. The reaction solution was added over 49 minutes to mixture of DI water (630 mL) and dimethoxyethane (42 mL) under vigorous stirring. The obtained slurry was stirred for 30 minutes, then filtered via a Buchner funnel (Whatman #3 filterpaper). The solid residue was washed four times with DI water (100 mL each) and once with heptane (100 mL), then dried at 45° C. and >29 inches of vacuum for 9 hours. Phenserine base (74.4 g) was obtained as reddish solid in 96.2% yield and 95.1% purity.

Example 3

Phenserine Tartrate Synthesis

Under an argon atmosphere a solution of tartaric acid (17.12 g, 0.114 mol) in a mixture of anhydrous ethanol (131 mL) and DI water (3.3 mL) was added over 32 minutes to a slurry of phenserine base (35 g, 0.1037 mol) in a mixture of anhydrous ethanol (126 mL) and DI water (3.1 mL). After about 60 to 75% of the tartaric acid solution were added the reaction solution was seeded with phenserine tartrate (72 mg). The reaction mixture was stirred for 19 hours 15 minutes at room temperature then a mixture of isopropanol (490 mL) and water (12 mL) was added over 30 minutes. The slurry was stirred for 3.5 hours, the filtered via Buchner funnel (Whatman #3 filterpaper). The white residue was washed twice with isopropanol (100 mL), then dried at 45° C. and 29 in for 19 hours to give phenserine tartrate (38.62g) in 76% yield and 99.4% purity as a white solid.

What is claimed is:

1. A process of producing a phenserine compound of the Formula

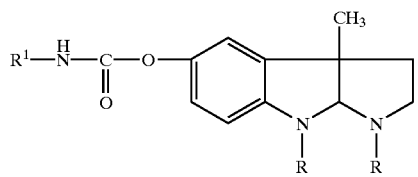

wherein R is a lower alkyl; and
$R^1$ is a cycloalkyl, phenyl, phenyl lower alkyl or cycloalkyl lower alkyl,
or a salt thereof comprising
a) treating a purified eseroline compound of the formula

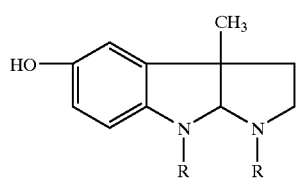

wherein R is as above
with a strong organic base in an anhydrous reaction medium containing an inert aprotic water miscible organic solvent; and b) reacting treated in said reaction medium, said treated eseroline compound with an isocyanate of the formula $$R^1\text{—}N\text{=}C\text{=}O \qquad V$$

wherein $R^1$ is as above,
by mixing said isocyanate with said reaction medium so as to form said phenserine compound.

2. The process of claim 1 wherein said water miscible solvent is a dimethoxyethane.

3. The process of claim 2 wherein said organic base is butyl lithium.

4. The process of claim 2 wherein R is methyl, and the isocyanate is phenylisocyanate.

5. The process of claim 1 comprising the additional step of adding water to the said reaction medium after formation of the phenserine compound to precipitate the phenserine compound formed in the reaction medium.

* * * * *